United States Patent [19]

Amplatz

[11] E Re. 29,343

[45] Reissued Aug. 9, 1977

[54] METHOD FOR FORMING AND STERILIZING CATHETERS

[76] Inventor: Kurt Amplatz, 10 Evergreen Road, St. Paul, Minn. 55110

[21] Appl. No.: 659,646

[22] Filed: Feb. 20, 1976

Related U.S. Patent Documents

Reissue of:

[64] Patent No.: 3,839,841
Issued: Oct. 8, 1974
Appl. No.: 271,586
Filed: July 13, 1972

[51] Int. Cl.[2] ..... B65B 55/18

[52] U.S. Cl. ..... 53/21 FC; 53/21 FW; 53/25; 53/29; 128/348; 264/320

[58] Field of Search ..... 53/21 FC, 25, 21 FW, 53/29; 128/348, 2 M, 2.05 R; 425/383, 392; 264/320, 322, 339

[56] References Cited

U.S. PATENT DOCUMENTS

| | | | |
|---|---|---|---|
| 1,573,023 | 2/1926 | Wrighton | 264/339 |
| 3,022,614 | 2/1962 | Dreyfus et al. | 53/30 |
| 3,043,067 | 7/1962 | Rynkiewicz et al. | 53/21 FC X |
| 3,612,038 | 10/1971 | Halligan | 128/348 X |

*Primary Examiner*—Travis S. McGehee
*Attorney, Agent, or Firm*—Burd, Braddock & Bartz

[57] ABSTRACT

A catheter for insertion into the human body and made of a thermoplastic tubing, is preformed to a desired shape by heating it above its free form temperature and allowing it to cool while held in that shape. To hold the catheter in position for such forming *and/or for storage before use*, a forming board having a catheter receiving groove of the desired shape is used. [The] *In the form of the invention shown, the* cross-sectional shape of this groove is wider at the bottom and narrower at the open top where it becomes a part of the board so as to hold the catheter in place during the forming and storage and to allow the catheter to be easily removed thereafter. This *particular form of* forming board is made by vacuum forming a sheet of thermosetting plastic *or thermoplastic material* over a solid, non-heat responsive, master representation of the exact longitudinal shape of the final preformed catheter. The cross-sectional shape of the master is the negative of the desired cross-section of the final forming board groove. When the catheter has been [so] preformed *and lies in one of the forming board grooves,* it and its forming board are packaged in a sealed plastic bag which is, like the catheter and the forming board, permeable to sterilizing gas. The resulting package is gas claved and stored in this sealed condition until ready for use. The catheter is removed from the sealed package and *from* the forming board immediately before insertion into the body. When it has served its purpose, it [is] *can be* removed from the body, cleaned, positioned back into [the] *a* forming board, preformed with heat when necessary, placed in another sealed film container, and resterilized for storage until it is again needed.

6 Claims, 8 Drawing Figures

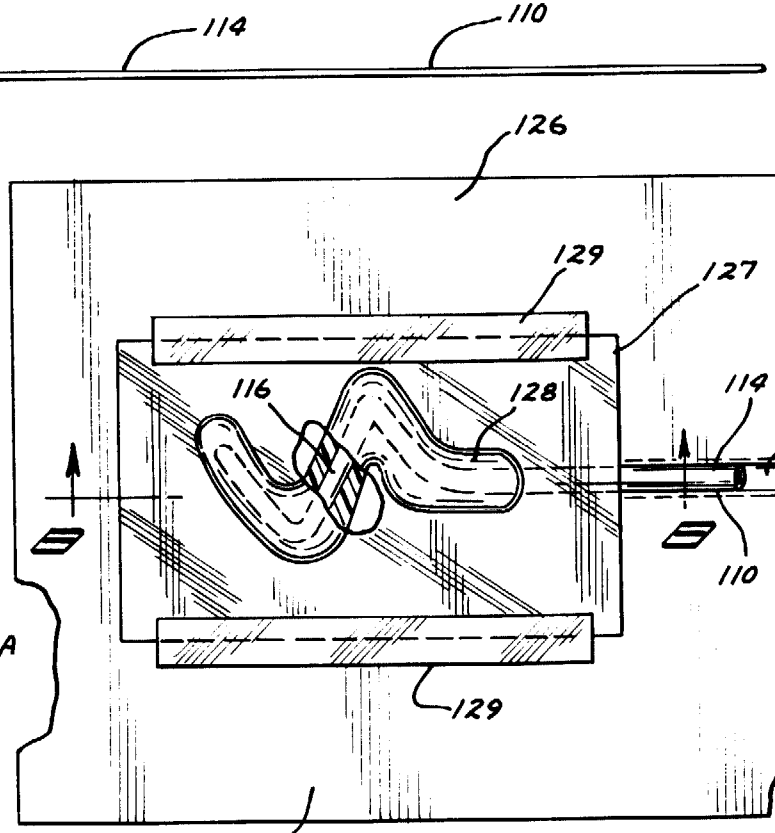
FIG. 5
FIG. 7
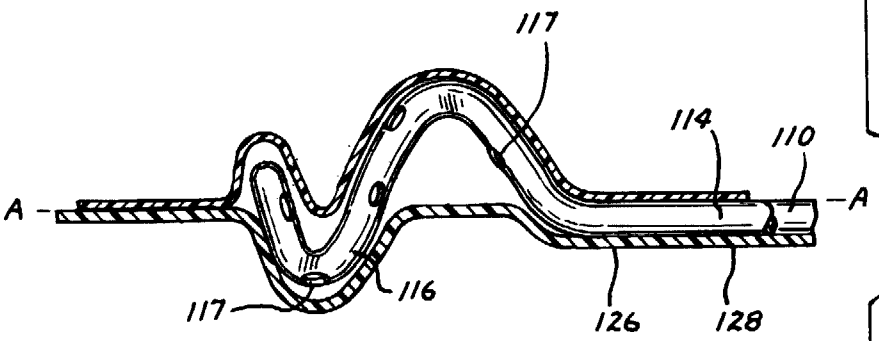
FIG. 8

METHOD FOR FORMING AND STERILIZING CATHETERS

Matter enclosed in heavy brackets [ ] appears in the original patent but forms no part of this reissue specification; matter printed in italics indicates the additions made by reissue.

BACKGROUND OF THE INVENTION

This invention relates to catheters of preformed shape for insertion into the human body for a variety of purposes, and to the manufacture of such catheters, the sterilization and storage of them until ready for use, and the reclamation, reworking and restorage of them for additional use.

Reuse of catheters of preformed shape before the present invention was difficult, and in many cases impossible, making it necessary to discard such a catheter after a single use. This was occasioned by the fact that the Freon or other gases used to sterilize the catheters tended to soften them and tended to cause them to lose their preformed shape. Also, many of the best materials for manufacture of these catheters become free form at around 100° C; and in cleaning and sterilizing the catheters for reuse, any time this temperature was reached or approached, the preformed shape of the catheter tended to be lost.

Before the present invention, in order to preform the catheter to the desired preformed shape so that it could be reused, it was necessary to insert a bendable, nonresilient wire through the center of the catheter, and to bend the wire and the catheter into what the technician or doctor considered the best preformed shape before sterilization thereof. This wire-catheter combination was then put inside of a gas permeable plastic bag which was sealed, and then put into a gas sterilizer or gas clave unit. In the sterilizer, the pressure was increased at least slightly above atmospheric, and the temperature raised to about the free form temperature of [100° C] *115° F.* The ethylene oxide or Freon, or other suitable sterilizing gas, was introduced into the sterilizer and allowed to permeate throughout the plastic bag, and through the side walls of the catheter. See U.S. Pat. No. 3,612,038, granted Oct. 12, 1971 to J. C. Halligan.

Unfortunately, there was no effective way to determine the action of the sterilizing gas medium on bacteria which would be lodged between the side wall of the catheter and the stiffening wire. Thus no positive assurances could be given that the sterilization was complete. Further, even though sterile, it was objectionable to introduce a wire into the catheter and then take it out just before the catheter was introduced into the body, because of the possibility that some deleterious material had adhered to the stiffening wire and would be scraped from it and thus would remain inside of the catheter.

In order to manufacture and to initially preform catheters before the present invention, solid metal plates were laboriously grooved out to form exact representations of both sides of the negative image of the catheters, and the catheters were confined in these aligned, facing, hemispherical grooves while they were heated to be preformed. This procedure was, of course, costly and unwieldy, and basically only usable at the point of manufacture of the catheter. Even so, these devices were somewhat effective. They were completely ineffective, however, in the manufacture of shapes which did not lie in a single plane. For example, production of a "pigtail" catheter, where the leading edge is shaped like a portion of a corkscrew, were impossible using the aforesaid method. Here only the stiffened insert wire method could be used, with its questionable sterilization practice and with its inaccuracy in forming and holding the desired shapes.

After catheters were properly formed by the old methods, it was extremely difficult to safely maintain them in a sterilized condition, to store them indefinitely and effectively until needed, and to transport them from the place of manufacture to the place of use. If, in storage or transportation, the catheters were bent out of the desired final preformed shape, any time they were accidentally subjected to [hear] *heat* [over 100° C] *about 115° F,* they would become free form, and when cooled again, would have the preset form of the shape in which they were stored rather than the shape in which they were formed. Even when catheters were cushioned between gauze layers and the like, and stored in boxes each large enough to completely encompass the catheter in its desired final form, three dimensional forms like the corkscrew form discussed above could not be protected and would tend to fall from their own weight when they were accidentally stored or purposely sterilized at a temperature approaching the free form temperature of the material of which they were made. Similar loss of shape tended to occur when the action of the sterilizing gas on them caused them to tend to lose their preformed stiffness.

BRIEF SUMMARY OF THE INVENTION

The above mentioned difficulties in the manufacture, storage, sterilization, use and reuse of catheters are all overcome by the method and structure and apparatus of the present invention.

Catheters are put inside of the body into various organs for various purposes. In the case of a catheter into the heart, for example, the leading 3 or 4 inches of the catheter are preformed to have a particular shape so that the catheter will go into the right place in the heart once it reaches the heart through a blood vessel. Such catheters must be flexible to follow a tortuous route into position, but should take on [the free form] *a predetermined* shape when they reach a point where they are not closely confined by the sides of the passageway through which they enter.

A forming board having a groove therein of the exact longitudinal configuration desired in the catheter is used. A length of suitable thermoplastic tubing is positioned in this groove, and the combined forming board and catheter unit are heated to a temperature at or above the free form temperature of the particular plastic making up the catheter tube. When the catheter cools down, it will be in, and will retain or come back to the preformed shape unless, before used, it is again heated to or above, or close to its free form temperature, or chemically softened by sterilization gases.

[The] *When the same forming board is to be used to sterilize and store the catheter, the* forming board groove, in addition to being the exact longitudinal shape of the desired final product, has a cross-sectional [shape] *configuration* which is generally pear-shaped. That is, a wider groove portion for confining the catheter tubing is situated on one side of the plane of the forming board, and a narrower [groove] portion suitable for preventing the tubing from accidentally falling out of the groove forms the top of the groove and ends integral with the board in the plane of the board.

In order to make a forming board of the exactly correct shape, a master representation of the exact longitudinal shape of the final catheter and of the cross-sectional shape of the desired forming board groove is mounted over a vacuum forming press bed, and the forming board is drawn down by the usual vacuum methods over the master. The plastic of the forming board being flexible, the master can be removed after the forming board has cooled in final shape and is ready for use in manufacture of catheters as explained above.

After the forming board and catheter have been raised to above the free form temperature of the plastic in the catheter and cooled to preform or preset the shape of the catheter, the resulting board-catheter unit can be sterilized and stored in a sealed plastic bag or otherwise until just before the catheter is to be used for its intended purpose of insertion into the body. The catheter and the forming board can be of a plastic which is permeable to sterilization gases, as can a plastic envelope into which the board-catheter unit is sealed. Where such a sealing envelope is impervious to air, the interior of the package including the board-catheter unit, will remain in sterile condition for an indefinite period.

After the catheter has served its intended purpose inside of the body and is withdrawn, it can be cleaned, reinserted in the same forming board or one having a similar or new desired groove shape, reheated to its free form temperature, and cooled, sterilized and packaged to be stored until it is again to be used.

Where preforming in three dimensions is necessary or desirable, two such boards can be made. The first board is drawn down over the master representation which has been set in a horizontal shape to appear above the floor. The second board is made by drawing down over a second remaining portion of the preformed shape which extends out of a similar horizontal floor.

IN THE DRAWINGS

FIG. 1 is a top plan view of a forming board with a catheter positioned in the forming groove.

FIG. 6 is an elevational view of a portion of a three dimensional preformed catheter;

FIG. 8 is an enlarged vertical sectional view taken on the line 8—8 in FIG. 7.

DESCRIPTION OF PREFERRED EMBODIMENTS

Typically, a catheter 10 consists of an attachment fitting 12 and a length of flexible tubing 14. A leading end portion 16 of this tubing is provided with suitable openings to allow ingress and/or egress to the catheter from the body once the catheter is properly positioned therein.

In some instances, there is no particular advantage to be gained by preforming the outer end portion 16 of the catheter, but the method and apparatus of the invention are still effective in the making, storing, sterilizing, and reforming of the catheter for reuse.

A particular problem presents itself, however, when it is necessary or desirable to preform the leading end portion 16 to a specific shape so that the catheter will naturally assume its proper position within the body once it is free of the confinement of the passageway through which it was introduced into the body. The present invention is particularly useful in overcoming this problem.

Figure 2:
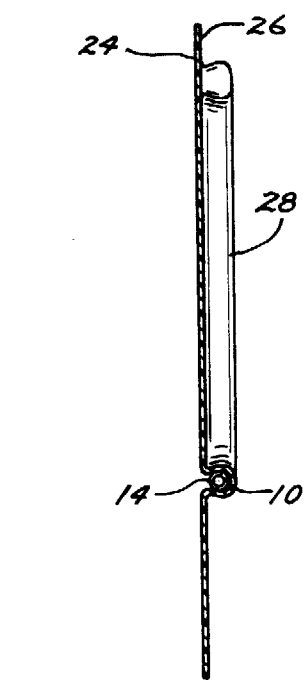
FIG. 2 is an enlarged sectional view taken on the line 2—2 in FIG. 1.
Figure 3:
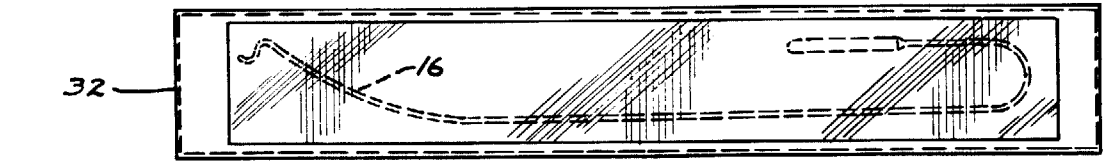
FIG. 3 is a plan view of the catheter and forming board unit of FIG. 1 on reduced scale and pictured inside of a transparent plastic envelope for sterile storage.
Figure 4:
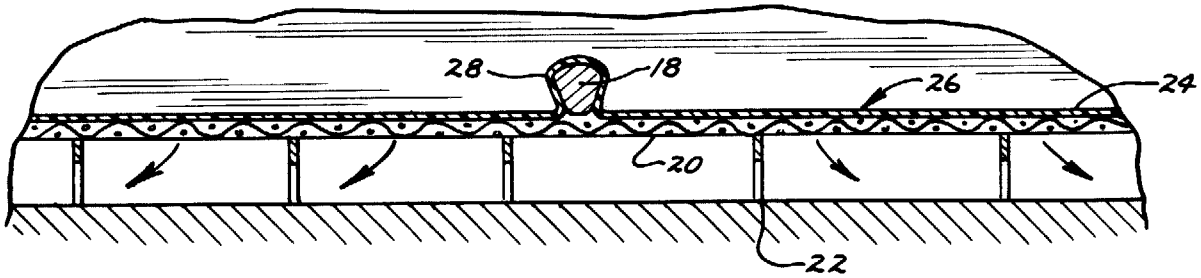
FIG. 4 is a fragmentary vertical sectional view of the forming board of FIGS. 1 through 3 in the process of being manufactured and showing its positioning on a fragment of a vacuum form press bed and encompassing a master representation of the desired catheter shape.
Figure 5:
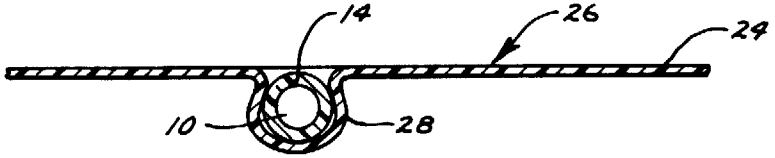
FIG. 5 is a further enlarged sectional view of a fragment of the forming board and catheter illustrating how the catheter is held in the forming board groove.

Assuming that it is desired to preform the end portion 16 of the catheter 10 as seen in FIGS. 1 through 3 into the shape as seen in FIG. 1, a non-heat responsive master representation 18 of the desired final longitudinal catheter shape is made up. The cross-sectional shape of this master 18 will be as seen in FIG. 4, where the master 18 is shown to be positioned on a screen 20 of a vacuum forming press bed 22. By any usual or preferred method, a thermosetting plastic sheet 24 is drawn down over the master 18, allowed to cool, and trimmed to the shape shown in FIG. 1 to constitute the forming board 26. Once the sheet 24 has cooled, it has sufficient flexibility so that it can be removed from the master 18, thus leaving an open pearshaped groove 28 as an integral part of the forming board 26, as clearly seen in FIGS. 2, 4 and 5. The forming board is made of plastic which, once set in the desired shape, is non-heat responsive at temperatures encountered in the preforming, sterilization and storage of the catheter. Sheets of polystyrene have been found excellent for the purpose.

Catheters are typically made from plastics which will become free form at around [100° C] *115° F.* Polyurethane, polyvinyl, and polyethylene, among other materials, have been successfully used.

To manufacture a catheter in accordance with the method of the invention, a forming board such as the board 26 is prepared *as* described above, the attachment fitting 12 is fastened to an appropriate length of flexible tubing 14, and the tubing forced into the groove 28 of the forming board 26 to have position as seen in FIG. 1.

This resulting forming board-catheter unit is then heated in an appropriate oven or otherwise to or above the free form temperature of the tubing, and allowed to cool to substantially below that temperature.

[The] *Such a* board-catheter combination is inserted into a plastic envelope 30 of polyvinyl or other appropriate material, which is then hermetically sealed as at 32.

The catheter, board, and envelope are of materials which are permeable to the usual sterilizing gases such as ethylene oxiode or Freon, and the package is put into a gas clave where the temperature and pressure are elevated to cause the gas to completely permeate the catheter, forming board and, of course, the envelope. When removed from this gas clave, this catheter package can be stored indefinitely and will remain in sterile condition until such time as it is to be used. The gases used in sterilization often have a tendency to soften the plastic of the catheter, and so the fact that the catheter is supported at all times in the groove 28 of the forming board 26 insures that the desired preformed shape will not be lost. Also, should the temperatures to which stored packages are subjected reach or approach the free form temperature of the catheter, the shape of the catheter will not change, and when the temperature again drops into a more normal range, the catheter will still have the desired preformed shape.

When the catheter is to be used, the sterile envelope package will be opened, the forming board and catheter removed, the catheter removed from the forming board and inserted into the body as needed. When it has served its purpose in the body, it will be removed, and can be cleaned. To reshape it to insure that it will have the same preformed shape for reuse or to give it any other desired preformed shape, it is again inserted in a groove [28] in an appropriate forming board, and the board-catheter unit again brought up to the free form temperature of the plastic in the catheter[.] *and allowed to cool to substantially below that temperature.* After being sealed in an envelope as previously explained, it can be resterilized, and stored until ready for further use.

Figure 7:
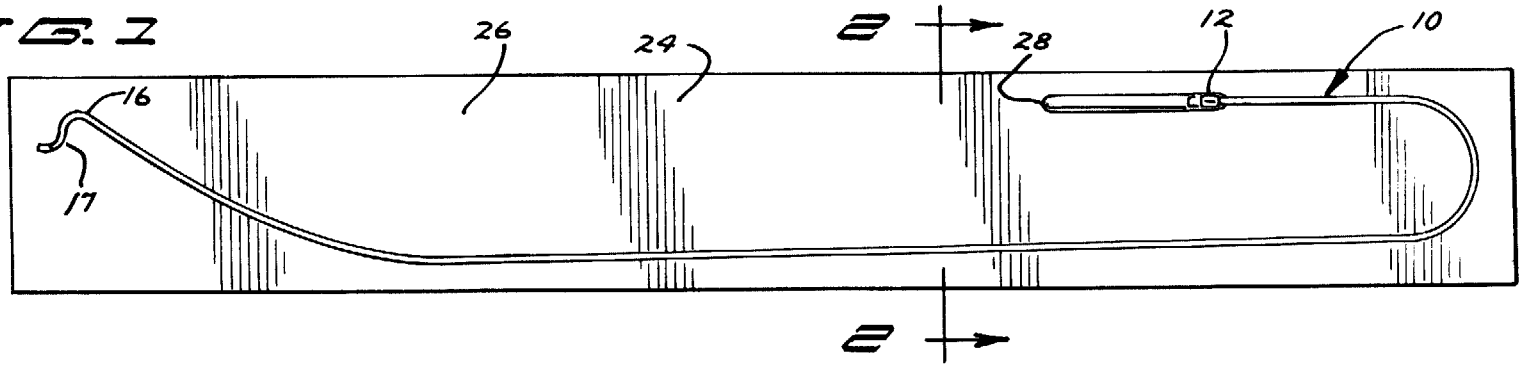
FIG. 7 is an elevational view of the three dimensional end portion of the catheter of FIG. 6, a portion of a first forming board and the second forming board used in initially preforming the catheter, holding it during sterilization and storage, and reforming it when this should be necessary or desirable.

Referring now to FIGS. 6 through 8, a three dimensional catheter 110 includes flexible tubing 114 and a three dimensional "corkscrew" or "pigtail" leading end portion 116 having ingress and/or egress orifices 117 therein.

In order to prepare a pair of matching forming boards to position the catheter in the performance of the method described in connection with FIGS. 1 through 5, a master representation of the longitudinal shape of the desired finished catheter and of the appropriate pear-shaped cross-sectional form will be prepared. While such a master representation is [now] *not* shown in the drawings, it will very closely approximate the shape of catheter 110. The master representation will be associated with a plane, vacuum forming press bed screen surface similar to the surface of screen 20 in the first form of the invention in such a manner that the portion of it corresponding to the portion of catheter 110 shown below the plane A—A in FIG. 8 will be above the screen so that a first forming board 126 can be made by the method described in connection with the first form of the invention. After that board is made, the master representation will be associated with a vacuum forming press bed screen in such a manner that the portion of leading end portion 116 of the catheter above plane A—A in FIG. 8 will be above the screen, so that a second forming board 127 can be made. Both of these boards have grooves 128 therein which are shaped to retain a catheter until such time as the catheter is forcibly removed therefrom.

Once these forming boards 126 and 127 are made, an appropriate length of flexible catheter tubing 114 will be snapped into place in the groove 128 of board 126, leaving an appropriate length to complete the loops of end portion 116 sticking out at the proper place. This protruding portion is encompassed by the groove 128 in second forming board 127, and, as shown in FIG. 7, pressure sensitive adhesive strips 129 are used to temporarily fixedly position the two boards with respect to each other to support the catheter in its three dimensional form. The resulting forming board-catheter unit are then heated to the free form temperature of the plastic in the catheter and allowed to cool, thus preforming the desired three dimensional shape in the leading end portion 116, as clearly seen in FIGS. 6, 7 and 8.

This board-catheter unit will then be encompassed in an envelope, such as the envelope 32 in connection with the first form of the invention, the resulting package hermetically sealed, and sterilized and stored until the catheter is to be used.

After the catheter has served its purpose in the body and is removed, it may be cleaned up and utilized in the same forming boards, or it can be utilized in other appropriate forming boards to preform other desired shapes.

I claim:

[1. A method of forming into a predetermined shape an elongated strip of thermoplastic material having a temperature above which it is free forming and below which it tends to retain its shape, the method including the steps of:

1. preparing a forming board having a groove of shape to support a catheter in a predetermined desired configuration;
2. supporting the catheter in said groove to constitute a forming board-catheter unit;
3. heating this unit at least to the free form temperature of the catheter material; and
4. reducing the temperature of the unit to substantially below the free form temperature.]

2. A method of making and preserving in readiness for use a catheter for use within the human body, *said catheter comprising an elongated strip of thermoplastic material having a temperature above which it is free forming and below which it tends to retain its shape, the method* including the steps [enumerated in claim 1, followed by the following steps] *of*:

*1. preparing a forming board having a groove of shape to support a catheter in a predetermined desired configuration;*

*2. supporting the catheter in said groove to constitute a forming board-catheter unit;*

*3. heating this unit at least to the free form temperature of the catheter material;*

*4. reducing the temperature of the unit to substantially below the free form temperature;*

5. encompassing the forming board-elongated strip unit in a hermetically sealed envelope;
6. sterilizing the interior of the envelope and the contents thereof; and
7. retaining the catheter in the forming board and in the envelope until it is ready to be used.

3. The method of claim 2 wherein the steps of supporting the catheter in the groove consists of constituting the groove as of pear-shaped configuration in cross section, the groove opening to the surface of the forming board, and having a top surface dimension less than that of the normal diameter of the catheter, and having a larger, lower, dimension sufficient to encompass the catheter.

4. The method of claim 2 wherein the forming board has been prepared to have a groove of shape to support a catheter by preparing a master having such predetermined desired configuration, setting this master on an air permeable base, heating a sheet of thermosetting plastic, and drawing it down on the master and the base by vacuum forming methods, allowing it to cool and removing it from the base and the master from it.

*5. A method of preparing and preserving in readiness for use a catheter for use within the human body, said catheter*

*comprising an elongated strip of thermoplastic material having a temperature above which it is free forming and below which it tends to retain its shape, the method including the steps of:*

*1. preparing a forming board having a groove of shape to support a catheter in a predetermined desired configuration;*

*2. supporting a catheter in said predetermined desired configuration;*

*3. heating the catheter at least to the free form temperature of the catheter materials;*

*4. reducing the temperature of the catheter to substantially below the free form temperature;*

*5. supporting the catheter in said groove of said forming board to constitute a forming board catheter unit;*

*6. encompassing the forming board-elongated catheter unit in a hermetically sealed envelope;*

*7. sterilizing the interior of the envelope and the contents thereof; and*

*8. retaining the catheter in the forming board and in the envelope until it is ready to be used.*

*6. The method of claim 5 wherein the forming board has been prepared to have a groove of shape to support a catheter by preparing a master having such predetermined desired configuration, setting this master on an air permeable base, heating a sheet of thermosetting plastic, and drawing it down on the master and the base by vacuum forming methods, allowing it to cool and removing it from the base and the master from it.*

*7. The method of claim 5 wherein the steps of supporting the catheter in the groove of the forming board consists of constituting at least part of the groove as of pear-shaped configuration in cross-section, the groove opening to the surface of the forming board, and having a top surface dimension less than that of the normal diameter of the catheter, and having a larger, lower, dimension sufficient to encompass the catheter.*

* * * * *